United States Patent [19] [11] Patent Number: 5,007,937
Fishman et al. [45] Date of Patent: Apr. 16, 1991

[54] STRUCTURE FOR ENHANCED RETENTION OF ARTIFICIAL LIMBS AND METHOD OF FABRICATION

[75] Inventors: Sidney Fishman, New York; William Lembeck, Forest Hills, both of N.Y.

[73] Assignee: New York University Medical Center, New York, N.Y.

[21] Appl. No.: 175,828

[22] Filed: Mar. 31, 1988

[51] Int. Cl.$^5$ .............................................. A61F 2/80
[52] U.S. Cl. ...................................................... 623/34
[58] Field of Search ...................... 623/34, 36, 37, 35, 623/33; 2/59, 61, 62

[56] References Cited

U.S. PATENT DOCUMENTS

| 1,117,725 | 11/1914 | Tullis | 623/37 |
| 2,244,871 | 6/1941 | Guinzburg | 2/59 |
| 2,634,424 | 4/1953 | O'Gorman | 623/37 |
| 4,036,220 | 7/1977 | Bellasalma | 2/59 |
| 4,069,600 | 1/1978 | Wise | 2/61 X |
| 4,655,779 | 4/1987 | Janowiak | 623/37 |

FOREIGN PATENT DOCUMENTS

| 2587617 | 3/1987 | France | 2/61 |
| 267988 | 3/1927 | United Kingdom | 623/34 |

Primary Examiner—Randall L. Green
Assistant Examiner—David H. Willse
Attorney, Agent, or Firm—Darby & Darby

[57] ABSTRACT

An air impermeable sealing band of rubberized material is introduced between the patient's stump and the interior of a stump-receiving socket of an artificial limb, in one of two ways, depending on whether or not the patient wears a stump sock. If the patient wears a stump sock, the band of sealant material is impregnated into the stump sock. If the patient does not wear a stump sock, an impregnated sock is incorporated into the interior structure of the socket of the patient's prosthesis. The impregnated sock itself is fabricated by placing a conventional stump sock on a somewhat oversized form. An appropriate annular region on the sock is then masked off by means of tightly fitting plastic bags, and one of the plastic bags provides an enclosing outer sheath which encompasses the annular region and extends upwardly above the form. A rubberized material in liquid form is introduced through the top of the outer sheath and a vacuum is introduced below to draw the material into the annular region of the sock, so as top impregnate the same. The rubberized material penetrates the sock, is worked into an axially contoured shaped, and is then permitted to set. A stump-receiving socket for an artificial limb with an integral annular seal is fabricated by placing a stump sock with the seal on a cast of a patient's leg and then laminating the socket over the sock using conventional procedures for manufacturing stump-receiving sockets.

7 Claims, 3 Drawing Sheets

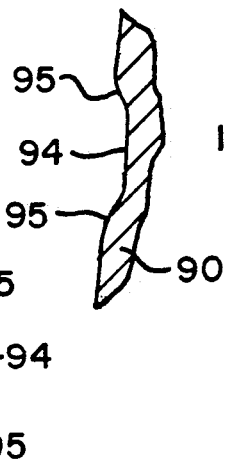
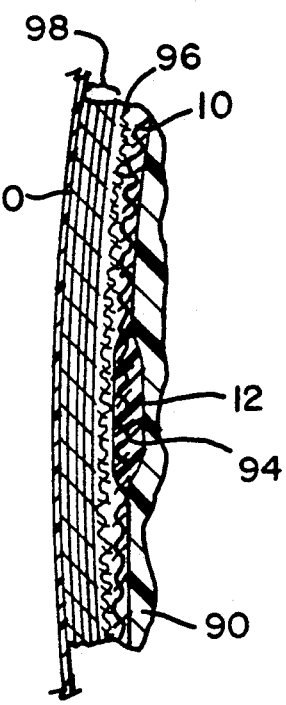
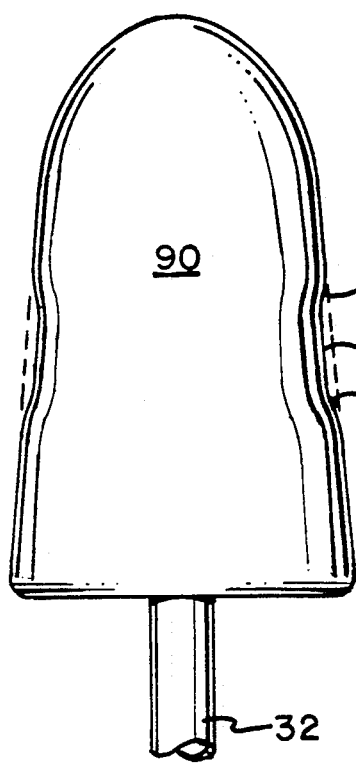
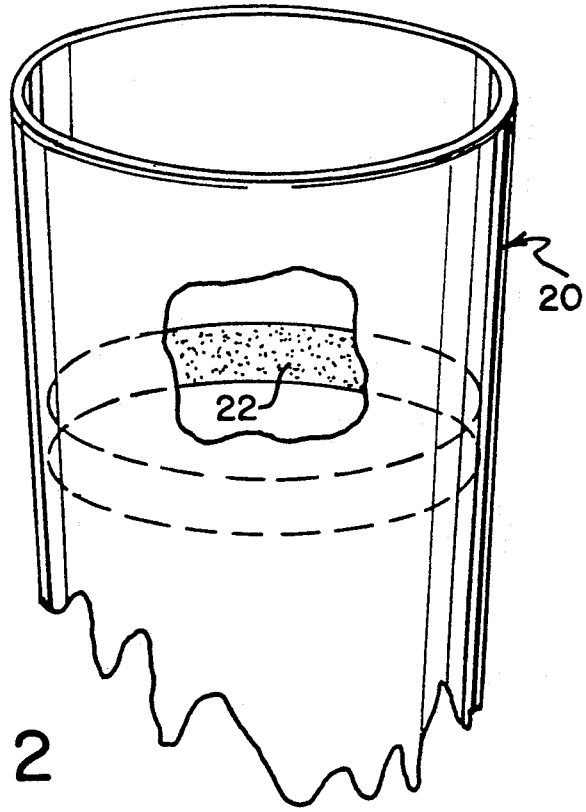
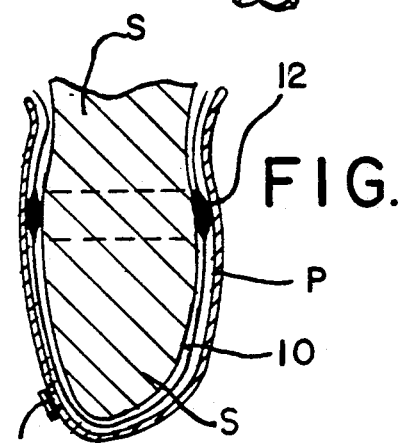
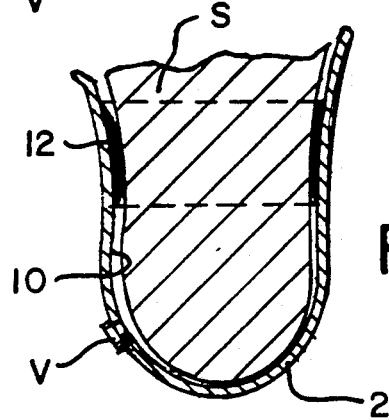

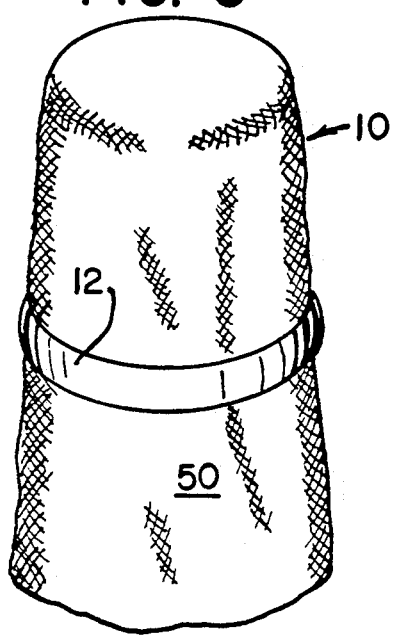
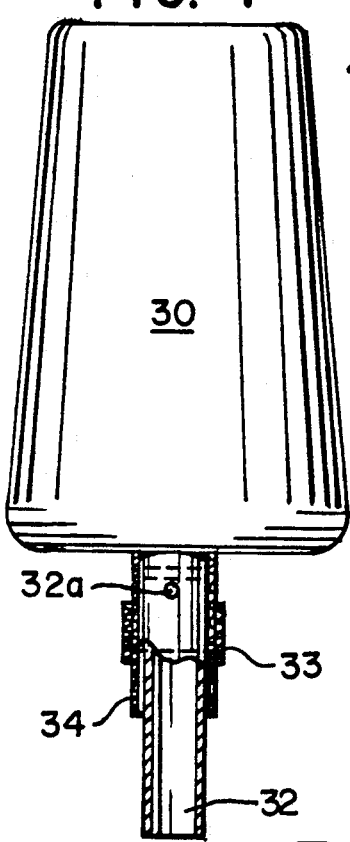
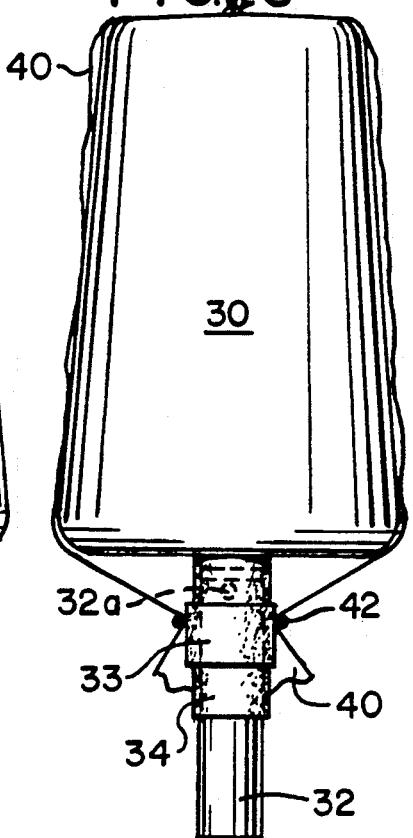
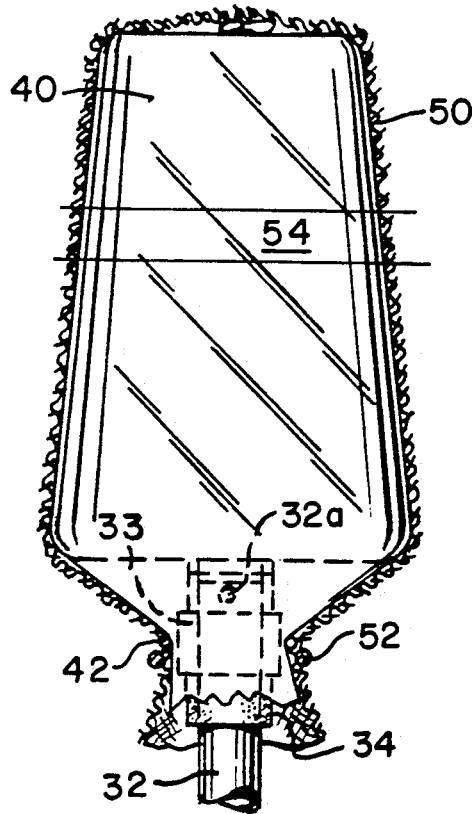
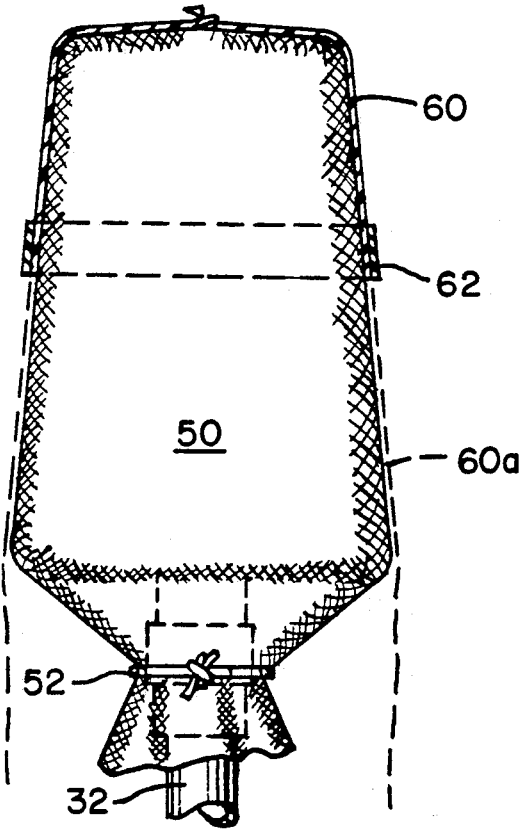

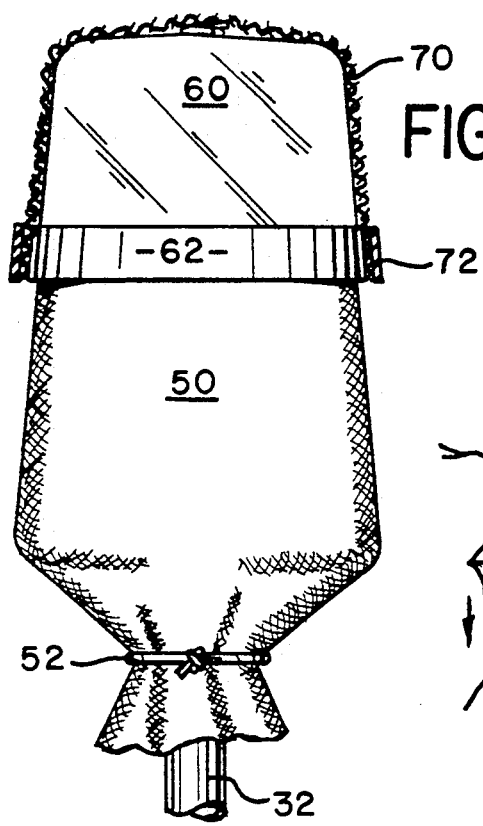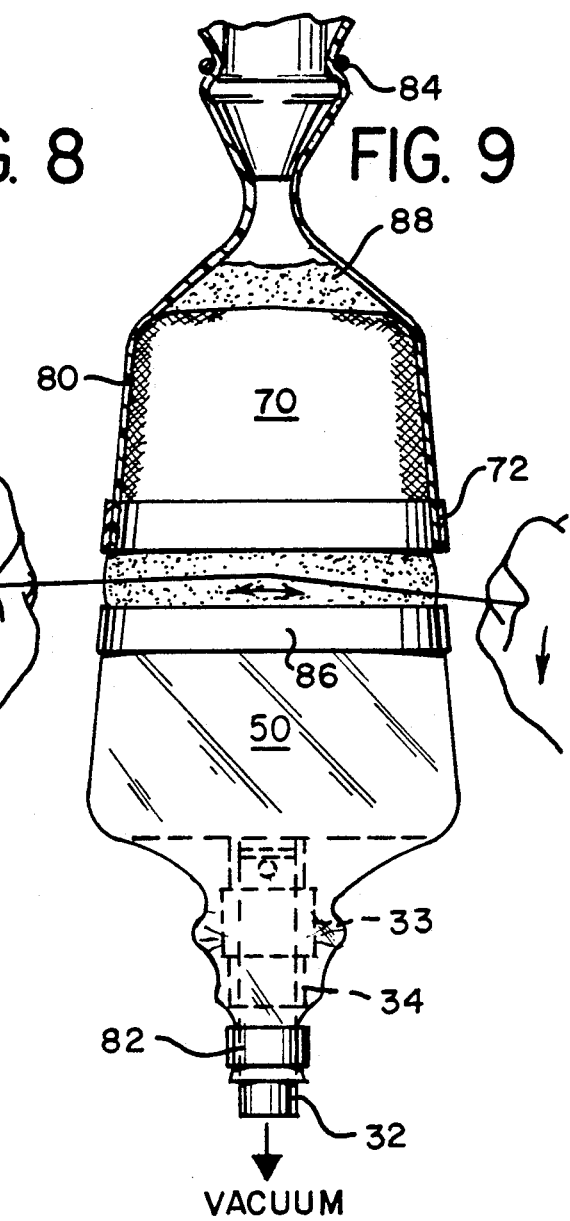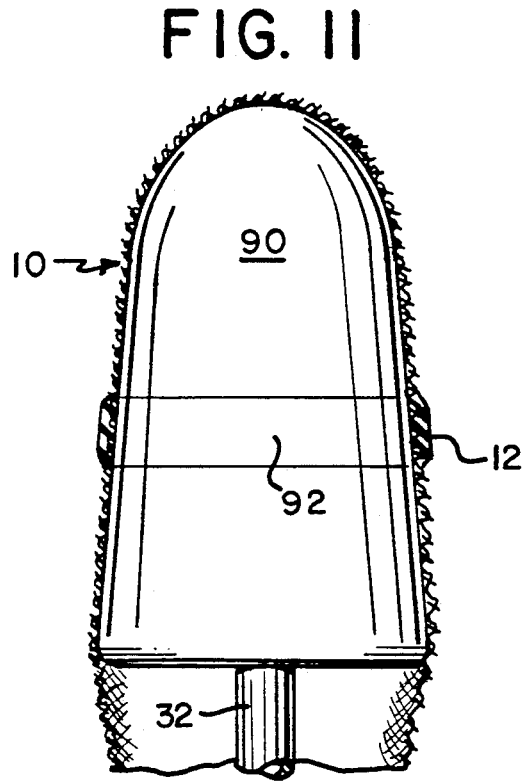

ature of a residual above-knee stump, in conjunction with tightly fitting proximal socket walls serves as a seal to preserve a partial vacuum within the socket. In the case of other amputees whose belowknee, upper-limb and other above-knee residual limbs lack the prerequisite characteristics, it has been impossible to use suction successfully with any frequency, because of the tendency for gaps and channels to form between the stump and the socket walls with a resultant loss of suction or partial vacuum within the socket.

STRUCTURE FOR ENHANCED RETENTION OF ARTIFICIAL LIMBS AND METHOD OF FABRICATION

FIELD OF THE INVENTION

The present invention relates generally to artificial limbs and, more particularly, concerns a prosthetic socket for use in an artificial limb and a sock to be worn in a prosthetic socket, which provide an air seal, to retain the socket on the residual limb of a patient by means of differential atmospheric pressure. The present invention also relates to methods of fabricating a stump-receiving socket for an artificial limb and a prosthetic stump sock so as to achieve the air sealing.

BACKGROUND OF THE INVENTION

It has long been appreciated that differential air pressure may be utilized to retain a prosthetic limb on a patient's limb or stump. Gravitational and other forces tend to cause separation between the prosthetic limb and the patient's residual extremity during use. This happens, for example, during the swing phase of gait, when a prosthetic leg is additionally subjected to centrifugal forces. Patients have routinely worn a variety of belts, straps, cuffs and harnesses to retain their prosthetic limbs against separation from the residual limb. In addition, a variety of socket configurations have been utilized for the same purpose. However, none of these can provide the reliable, strong retentive force which is provided by differential air pressure in accordance with the present invention.

For many years differential air pressure or "suction" sockets have been utilized with reasonable success in prosthetic limbs for selected above-knee amputees. However, there has been a corresponding lack of success in using such sockets for other levels of amputation. The basic reason for this is that the relatively soft, fleshy characteristics of a residual above-knee stump, in conjunction with tightly fitting proximal socket walls serves as a seal to preserve a partial vacuum within the socket. In the case of other amputees whose belowknee, upper-limb and other above-knee residual limbs lack the prerequisite characteristics, it has been impossible to use suction successfully with any frequency, because of the tendency for gaps and channels to form between the stump and the socket walls with a resultant loss of suction or partial vacuum within the socket.

Most amputees wear woven "stump socks" as an interface between their skin and the prosthetic socket for increased comfort, perspiration absorption, and reduced friction. These socks vary from thin sheaths (about 0.010–0.015 inches thick) to rather thick socks (about 0.125 inches thick) which are used to accommodate substantial discrepancies between stump shapes and volumes in relation to the prosthetic socket. All of these socks, regardless of the material from which they are fabricated (nylon, orlon, cotton, wool, etc.) are porous. As such, air flows freely past the proximal borders of the socket, making it impossible to maintain a vacuum within. The same problem of uncontrolled air leakage can exist when no stump sock is worn.

Broadly, it is an object of the present invention to overcome the shortcomings of known artificial limbs utilizing differential air pressure, which shortcomings result in the inability to reliably and consistently retain the prosthesis on the patient's residual limb. It is a specific object of the present invention to create an air seal between the socket of the prosthesis and the residual limb, so that air leakage and the accompanying loss of vacuum may be avoided. As a result, a great many well-fitted prosthetic sockets may be used in the same manner as a suction socket, when the patient wears a prosthetic sock in accordance with the present invention.

It is another object of the present invention to provide a prosthetic sock, which may be worn by a patient over his stump, in order to provide consistent and reliable air sealing between the socket of the prosthesis and the patient's stump, thereby making it possible to retain a great many wellfitted artificial limbs by means of differential air pressure.

It is another object of the present invention to provide an improved construction for the stump-receiving socket of an artificial limb which will provide a consistent and reliable air seal between the socket and the patient's stump, regardless of the characteristics or morphology of the stump.

It is yet another object of the present invention to provide a method for fabricating a prosthetic sock and a stump-receiving socket for an artificial limb in accordance with the two immediately preceding objects.

It is also an object of the present invention to provide a stump-receiving socket for an artificial limb, a prosthetic sock useful in retaining well-fitted artificial limbs, and a method for manufacturing the same, which are reliable and convenient in use, yet relatively inexpensive.

In accordance with the present invention, an air impermeable, elastic sealing band is introduced between the interior of the stump-receiving socket and the patient's stump in one of two ways, depending on whether or not the patient wears a stump sock. If the patient wears a stump sock, the sealing band is impregnated into the stump sock. If the patient does not wear a stump sock, the impregnated sock is incorporated into the structure of the socket of the patient's prosthesis.

The impregnated prosthetic sock itself is preferably fabricated by placing a conventional stump sock on a somewhat oversized cylindrical or conical form shaped generally like the stump. An appropriate annular region on the sock is then masked off by means of tightly fitting plastic bags, and one of the plastic bags provides a enclosing outer sheath which encompasses the annular region and extends upwardly above the form. A rubberized material in liquid form is introduced through the top of this outer sheath bag, and a vacuum is introduced below to draw the material into the annular region of the sock so as to impregnate the same. The rubberized material penetrates the sock, is worked into an axially contoured shaped, and is then permitted to set. After the sealant material is fully cured, the plastic bags may be discarded and the sock removed from the form.

A stump-receiving socket with an integral annular seal is preferably fabricated by placing a prosthetic sock with an impregnated seal on the cast of a patient's residual limb and then forming the stump-receiving socket, by lamination, over the sock using conventional procedures for manufacturing sockets.

BRIEF DESCRIPTION OF THE DRAWING

The foregoing brief description, as well as further objects, features and advantages of the present invention will be understood more completely from the following detailed description presently preferred, but nonetheless illustrative embodiments of the present invention, with reference being had to the accompanying drawing in which:

FIG. 1 illustrates the manner of using a stump sock in accordance with the present invention;

FIG. 2 illustrates the manner of using a laminated stump-receiving socket in accordance with the present invention;

FIG. 3 is a perspective view of a stump sock with an annular sealing band fabricated in accordance with the present invention;

FIG. 4 illustrates an initial step in the fabrication of the prosthetic sock, whereby a form and mandrel have been prepared to receive a conventional stump sock;

FIG. 5 illustrates a subsequent step in the fabrication process, there a plastic bag has been placed over the form and mandrel and secured below the bottom of the form;

FIG. 6 illustrates the next step, according to which the stump sock is pulled over the form and secured therebelow;

FIG. 7 illustrates a subsequent step, whereby a second plastic bag has been pulled over the stump sock and trimmed to a level corresponding to the intended upper axial extreme of the annular sealing band;

FIG. 8 illustrates a subsequent step in which a tubular sock is placed on top of the second plastic bag;

FIG. 9 illustrates the complete lay-up of the form, after a third plastic bag which is open at the top has been drawn over the entire stump sock, secured therebelow to form an outer sheath thereabout, and taped at a level corresponding to the lower axial extreme of the desired annular sealing band, with a liquid rubberized material having been introduced to the top of the third bag from above and drawn thereinto by means of a vacuum applied therebelow;

FIG. 10 is a perspective view of a prosthetic socket with an integral internal annular sealing band in accordance with the present invention;

FIG. 11 illustrates how the prosthetic sock is positioned on the cast to mark the location of the groove;

FIG. 12 illustrates a cast of the patient's residual limb, after the cast has been prepared for the fabrication of a stump-receiving socket with an internal sealing band in accordance with the present invention, by forming an annular groove therein;

FIG. 13 is a fragmentary sectional view of the cast of FIG. 11 illustrating the groove therein after further preparation for fabrication of the stump-receiving socket; and FIG. 14 is a sectional view, on an enlarged scale, illustrating the entire lay-up over the cast, immediately after the stump-receiving socket has been formed by means of a conventional lamination process.

DETAILED DESCRIPTION OF PREFERRED EMBODIMENTS

Referring now to FIG. 1, there is illustrated the method of utilizing a prosthetic sock in accordance with the present invention in a conventional stump-receiving socket. A stump sock 10 in accordance with the present invention is smoothly stretched over the stump S. Sock 10 has an impregnated annular seal 12 made of an air impermeable, elastic material, which preferably extends both exteriorly and interiorly of the sock. For the patient's comfort, the sealing band should extend primarily exteriorly of the sock. The sock has preferably been impregnated with a rubberized material by means of the process described below or an equivalent process to form sealing band 12. The sealing band is preferably 1-2 inches wide and preferably no more than 3/32 of an inch thick at its thickest point. Preferably, the sealing band should also be feathered to a negligible thickness at its upper and lower extremities.

The sealing band should be placed as proximally as possible with respect to the stump-receiving socket P (i.e. as high as possible on the patient's stump). Preferably, it is positioned within the top third of the sock, but it may occasionally be in the middle third. The precise dimensions and location of the annular band will depend on the nature of the sock and the socket being used, as well as the specific anatomy of the patient's stump, which differs with various levels of amputation and different individuals. When properly fabricated, the seal 12 provides an effective seal between the stump S and the socket, once the patient's stump is inserted. The sock 10 may therefore be used with well-fitted sockets that are not suction sockets and will convert the socket to a suction socket, by the simple addition of a one-way air valve to the socket. Under these circumstances, the patient may also utilize a shoe horn, or similar device, to break the air seal during insertion and removal of the stump from the artificial limb, if no air valve is added.

FIG. 2 illustrates a stump-receiving socket 20 with an integral annular sealing member in accordance with the present invention. As will be explained more fully below, the socket 20 is preferably fabricated by forming it directly over a prosthetic sock in accordance with the present invention, utilizing conventional lamination procedures.

As will be appreciated from FIGS. 1 and 2, the inner sealing band 12 acts as an air-tight seal over a substantial distance prior to the full insertion of stump S into the socket. As the patient's stump is inserted further into the socket, air pressure builds up under the stump. This air escapes from the socket by means of a conventional one-way valve V. This valve allows entrapped air to escape to the outside and then closes automatically when the pressure equalizes, thereby blocking reentry of air into the socket. As a result, when the stump is completely inserted in the socket, the air pressure is equal inside and outside the socket. Any tendency to remove the stump from the socket would increase the space between the inner socket wall and the stump, reducing the pressure inside the socket, since external air is unable to enter. The difference between air pressure and the reduced pressure within the socket then acts to maintain the socket on the stump. Those skilled in the art will appreciate that valve V would include a control to retain it open, in order to permit removal of the stump.

Owing to the ready availability of stump socks, the process of the present invention would preferably makes use of such devices as the basic stump cladding between the stump and the socket. However the use of stump socks is only illustrative, and it is contemplated that the stump cladding may be made of essentially any sheet material formed into a layer between the patient's stump and the socket.

The fabrication process for prosthetic sock 10 will be described, for illustrative purposes, with respect a conventional stump sock for a typical below-knee amputee. Owing to the irregular bony characteristics of below-knee stumps, these are the most difficult cases on which to effect suction retention. Subsequently, there will be described a process for manufacturing a stump-receiving socket with an integral sealing band. In every case, the stump sock with the impregnated sealing band must be fabricated as a preliminary step to this latter process. In addition, the fabrication procedures for stump socks and sockets in accordance with the present invention for all other levels of amputation are very similar to those that will be described, but the devices will vary in their dimensions and location of the sealing band, as well as the characteristics of the stump sock used.

In manufacturing the stump sock 10 with an impregnated sealing band, use is made of a somewhat oversized form that matches the shape of the stump sock. This is not a model of any particular patient's stump, but is more in the nature of a cylindrical or conical shape of the right general size. In general, different forms would be used for very different size socks. In any event, the form should be sufficiently large so that the sock is moderately stretched when it is placed over the form.

In referring to locations on the form, the socks, and the stump-receiving socket, the stump itself will be used as a reference. That is, the end of the sock and socket which are the most proximal when worn on the stump will be referred to as the proximal ends and vice versa. When the sock and socket are worn by the patient, the proximal end is uppermost, assuming the patient is standing. On the other hand, the sock and socket are normally fabricated in an inverted position, so that the proximal end is then lowermost. Accordingly, the bottom of the form would be considered the proximal end. Consistent use of the terms "proximal end" and "distal end" will therefore avoid any confusion.

As may be seen in FIG. 4, the form 30 for the fabrication of a prosthetic sock 10 in accordance with the present invention is provided with a pipe mandrel, preferably made of half-inch pipe and protruding approximately 6 inches from the proximal end of the form. Radial holes 32a, preferably ⅛ inch in diameter, are drilled in the pipe 32 in close proximity to the form. The precise position of these holes is of no importance. A strip of porous material is wrapped repeatedly around the pipe just proximal to the form, for example to a thickness of approximately ⅛ of an inch. This strip forms the wick 34 and preferably extends for approximately 3 inches along the pipe. The wick is secured by means of an additional strip of fabric 33, which is secured about it. The purpose of wick 34 will be discussed more fully below.

As may be seen in FIG. 5, the first plastic bag, preferably made of polyvinyl alcohol (PVA) is pulled down tautly over the form and is knotted at the distal end. The bag is again pulled taut, and the proximal end is tied down by means of a band 42 at approximately the midpoint of the wick 34. The remainder of bag 40 just distal to band 42 is then trimmed off (compare FIGS. 5 and 6).

As may be seen in FIG. 6, a conventional stump sock 50 is then stretched tautly over the PVA bag 40 and is tied down approximately at the midpoint of wick 34 by means of a band 52. A horizontal band area 54 of the desired width is then marked off lightly around the circumference of the sock 50. To assist in understanding, portions FIG. 6 are shown in section.

Next, as shown in FIG. 7, a second PVA bag 60 is pulled tautly over the stump sock 50 Bag 60 is knotted at its distal end and again pulled tautly, with stretched tape 62 being applied tautly around bag 60 so that its lowermost edge is aligned with the distal extreme of the marked off band area 54 The proximal portion 60a of bag 60 beyond the stretch tape 6 is then carefully trimmed off, as is the portion of the bag distal to the knot.

Referring to FIG. 8, a sheer nylon tubular "kneehigh" sock 70 is then applied over bag 60 and is pulled taut. Stretch tape 72 is applied tautly about the perimeter of sock 70, so as to overlie tape 62. The proximal portion of kneehigh 70 beyond the tape 72 is then carefully trimmed off. Sock 70 is provided in order to avoid substantial sliding friction between bag 60 and any plastic bags which are subsequently applied thereover Such sliding friction would make it difficult or impossible to pull an additional bag tautly over bag 60.

A third PVA bag 80 is then applied over the entire structure and pulled taut (see FIG. 9). Bag 80 is tied by means of a band 82, at a point proximal to wick 34 so a to encapsulate the wick. The distal end of bag 80 is attached to a funnel by means of an appropriate band 84. Stretch tape 86 is then applied tautly about the bag 80 so that its upper most edge aligns with the proximal most edge of band area 54 marked on sock 50.

The layup for impregnating sock 50 with a rubberized compound is now complete and will have the appearance of FIG. 9. A source of vacuum, such as a pump, is connected to the proximal end of the mandrel pipe 32 and, while the portion of bag 80 just below the funnel is pinched of with the fingers, vacuum is applied and adjusted to preferably 7 inches Hg.

Some discussion is warranted concerning how the vacuum is communicated from the pipe 32 to the upper portion of bag 80. It will be recalled that a porous wick 34 extends partially under bag 40 and sock 50 and that the proximal half of the wick is encapsulated by bag 80. When a vacuum is applied at the bottom of pipe 32, it is communicated to the wick through apertures 32a of the pipe 32. Inasmuch as the wick is porous, the vacuum is communicated under bag 40, as well as outside bag 40, through sock 50, and into the region between bag 80 and sock 50. Beneath bag 40, the vacuum serves to retain the bag securely against form 30. The vacuum within bag 80 is communicated upwardly within the bag and, therefore, appears at the funnel When the rubberized liquid material is poured into the funnel, it is drawn into bag 80 by the vacuum, but the downward travel of the liquid is interrupted by the tape 86. Liquid rubberized material accumulates under bag 80 distally of tape 86, and forms a reservoir of liquid 88 above sock 70. In the region above tape 86, liquid is drawn into sock 50, impregnating it. If necessary, additional rubberized liquid may be forced down to the region of tape 86 by squeezing the bag at the reservoir. After a sufficient quantity of the rubberized liquid is present in the region of the tape 86, that region is formed to a uniform thickness by means of "stringing". This is a procedure whereby an eight to ten inch length of string is held between the hands and is applied axially along the external contour of bag 80, in order to shape it properly or to move the rubberized liquid therein. During stringing, the diameter of the liquid material is measured with the calipers at the axial midpoint between the bands 72 and 86 (i.e. the region where the sealing band is to be formed). Stringing continues until a caliper measurement indicates that the diameter is three sixteenths of an inch larger than it was before the rubberized liquid was introduced (this, of course, assumes that a previous measurement of the diameter was taken). The diameter can be reduced by stringing liquid up towards the reservoir, or it can be increased by stringing liquid down form the reservoir. When the proper thickness of the rubberized liquid is present, the proximal and distal extremes of the soon-to-be sealing band are tapered down by stringing. Stringing may continue until the rubberized liquid material is nearly cured.

After the rubberized liquid material has fully cured, the outer layers overlying sock 50 are carefully removed from the impregnated sock, and then the sock is carefully removed from the form. The completed impregnated sock 10 then has the appearance of FIG. 3.

The rubberized liquid material is preferably a medical grade silicone elastomer, such as that available under the commercial name Ipocon 7. This is a two component product in which "Liquid A" is cured with either "Component B" or "Component B-quick", or a mixture of the two. The curing time can be varied from ½ hour using pure "Component B-quick" to 3 hours using pure "Component B". The hardness of the silicone can be varied by changing the ratio between the "Liquid A" and the curing mixture. In preparing the preferred silicone mixture, the mixing container is first weighed empty. Approximately 60 ml of "Liquid A" are poured into the container and the container is reweighed. Preferably, for every 7 grams of "Liquid A", one gram of "Component B-quick" is added, and the mixture is stirred well for half a minute. The mixture is then ready for pouring into the outer bag 80 of the layup for manufacturing sock 10. Initially, approximately half of the liquid may be squeezed out of the reservoir into the region of bag 80 above tape 86.

For those patients who do not wear stump socks, the present invention contemplates fabricating a stump-receiving socket with an integral, internal sealing band. FIG. 10 is a fragmentary perspective view of such a stump socket 20, with the sealing band being indicated by the reference character 22.

The first step in fabricating such a socket 20 is to fabricate a prosthetic sock 10 with an impregnated sealing band 12, as previously described. As is the common practice, the suction socket will be fabricated on a plaster model or cast of the amputee's stump. As may be seen in FIG. 11, the silicone impregnated sock 10 is stretched over the cast 90 so that the band 12 is properly located. The location of the distal and proximal edges of the band 12 are then lightly marked off on the plaster cast, to create a marked off area 92, and the stump sock 10 is then removed. As may be seen in FIG. 12, a channel 94 is then carved in the marked area 92 and the depth of the channel 94 is determined by the thickness of the silicone band 12. As indicated in the detailed fragmentary view of FIG. 13, the edges 95, 95 of channel 94 are then blended into the cast to avoid ridges or abrupt contours.

Cast 90 is similar to form 30 described above, in that it includes a similar pipe mandrel 32. The socket 20 is fabricated by a vacuum lamination process which is similar to the process described above with respect to FIGS. 4-9. Initially, the sock 10 is stretched over the cast 90 with the sealing band 12 being within groove 94. Sock 10 is then tied off to pipe 32. As shown in the fragmentary sectional view of FIG. 14, a dacron sleeve 96 is then pulled over cast 92 and sock 10. Thereafter, five layers of nylon stockinette 98 are pulled over the dacron sleeve and a PVA bag 100 is pulled over the stockinette layers 98. Like bag 80 of FIG. 9, bag 100 is open on top, and lamination proceeds in a similar manner by introducing a polyester or acrylic resin at the top of bag 100. This is drawn into the bag by means of a vacuum, similar to the process of FIG. 9. AFter the plastic has set, any excess laminate is trimmed off, and the plaster cast is carefully chiseled out to prevent any damage to the sealing band 12. The proximal area of the socket may then be trimmed and finished as required. The detailed procedures for laminating a suction socket are well known to those skilled in the art, and detailed descriptions thereof may be found, for ex ample, in the following references, the contents of which are incorporated herein by reference:

*Prosthetic Shop Manual*, American Orthotic and Prosthetic Association 1967;

*Manual of Below Knee Prosthetics*, Biomechanics Laboratory, University of California, November 1959;

*Adjustable-Brim Fitting of the Total Contact Above-Knee Socket*, Biomechanics Laboratory, University of California, March 1963.

With either the prosthetic sock or the socket of the present invention, air leaks may occasionally be discovered after the patient has donned his prosthesis. The sock or socket may readily be repaired at this time. As the initial step in the effecting the repair, the air leak is located and marked while the patient is wearing his prosthesis. If the patient is utilizing a sock in accordance with the present invention, then the sock is removed and stretched over a form. The sealing hand is cleaned with acetone and allowed to dry. Appropriate proportions of Ipocon body paste "component A" and "component B" are mixed together. The mixture is then applied with a spatula to the marked off areas to increase the thickness as required. The surface of this application is then smoothed with the spatula and the entire application is tapered own at the edges. AFter the paste has cured, the sock may be removed from the form and restored to service.

If the patient is utilizing a suction socket in accordance with the present invention, the prosthesis is removed, and a similar process to the preceding is followed in order to repair the integral sealing band.

Although preferred embodiments of the invention have been disclosed for illustrative purposes, those skilled in the art will appreciate that many additions, modification and substitutions are possible without departing from the scope and spirit of the invention as defined in the accompanying claims. For example, the sealing band need not be made of solid rubberized material, but could filled with a pressurized gas, such as air, or a liquid.

What is claimed is:

1. A prosthetic sock for use in a stumpreceiving socket of a patient's artificial limb, said sock comprising:
   an air permeable stump cladding interposed between the stump and the socket and having means at its distal end for limiting the degree to which the cladding may be drawn onto the patient's stump, said cladding having an open proximal end dimensioned to fit over the patient's stump; and
   an air impermeable, elastic, annular sealing band having an axial extent which is substantially less than that of said stump cladding said band being impregnated into and through said stump cladding so as to extend thereabout at an axial position calculated to achieve a sealing effect between the socket and the stump, at least, in a closed area at the bottom of the stump when it is inserted into said socket, the artificial limb being retained on the patient's stump substantially entirely by means of differential air pressure between the closed area and the exterior of the socket.

2. A prosthetic sock in accordance with claim 1 wherein said sealing band is located within the most proximal two-thirds of said sock.

3. A prosthetic sock in accordance with claim 1, wherein said sealing band is disposed axially within the most proximal one-third of said sock.

4. A prosthetic sock in accordance with claim 1, wherein said sealing band extends both within and outside said cladding.

5. A prosthetic sock in accordance with claim 1, wherein said sealing band is 1-2 inches wide in the axial direction and no more than 3/32 of an inch thick at its thickest point, said sealing band being tapered from its axial center towards its axial margins.

6. A prosthetic sock in accordance with claim 1, wherein said sealing band is made of a liquid, rubberized material which has been cured to a solid state.

7. A prosthetic sock in accordance with claim 6, wherein said rubberized material is a silicone elastomer.

* * * * *